United States Patent [19]
Hsu

[11] Patent Number: 5,753,706
[45] Date of Patent: May 19, 1998

[54] METHODS FOR TREATING RENAL FAILURE

[76] Inventor: Chen Hsing Hsu, 3720 Tremont Dt., Ann Harbor, Mich. 48105

[21] Appl. No.: 794,328

[22] Filed: Feb. 3, 1997

[51] Int. Cl.$^6$ ................................................ A61K 31/60
[52] U.S. Cl. ...................................................... 514/578
[58] Field of Search ........................................... 514/578

[56] References Cited

PUBLICATIONS

Chemical Abstract An 1995:828125, Kuroda et al, 1995.
Almaden, Y. et al., *Am. Soc. Nephrol* 6:957 (1995).
Brock, J. et al., *J. Pediat* 4:442–453 (1934).
Coburn, J.W. et al., *Kidney Int* 3:264–272 (1973).
Cox, G. et al., *J. Biol. Chem* 92:Xi–Xii (1931).
Deobald, H. et al., *Am. J. Physiol.* 111:118–123 (1935).
Gimenez, L. et al., *Kidney Int* 22:36–41 (1982).
Haut, L.L., *Kidney Int* 17:722–731 (1980).
Hollis B.W. et al., *Clin. Chem.* 32:2060–2063 (1986).
Hou, S.H. et al., *Am. J. Kidney Dis* 18:217–224 (1991).
Hsu, C., et al., *Kidney Int* 25:789–795 (1984).
Hsu, C.H. et al., *Kidney Int* 37:44–50 (1990).
Karlinsky, D. et al., *Kidney Int* 17:293–302 (1980).
Kilav, R. et al., *J. Clin. Invest* 96:327–333 (1995).
Lakshmanan, F.L. et al., *Am. J. Clin. Nutr.* 1368–1379 (1984).
Lau, K., *Kidney Int* 36:918–937 (1989).
Liu, S.H., et al., *Medicine*, Baltimore 22:103–161 (1943).
Lopez–Hilker, S. et al., *Am. J. Physiol* 259:F432–437 (1990).
Lumlertgul, D. et al., *Kidney Int* 29:658–666 (1986).
Martis, L., et al., *Perit Dial Int* 9:325–328 (1989).
Matkovic, V. et al., *Am. J. Clin. Nutr.* 55:992–996 (1992).
Naveh–Many, T. et al., *Am. Soc. Nephrol* 6:968 (1995).
Piraino, B. et al., *Clin. Nephrol* 37:48–51 (1992).
Portale, A.A. et al., *J. Clin. Invest* 73:1580–1589 (1989).
Ramirez, J.A. et al., *Kidney Int* 30:753–759 (1986).
Rehm, P. et al., *J. Nutrition* 19:213–222 (1940).
Reinhardt, T.A. et al., *J. Clin. Endocrinol Metab* 58(1):91–98 (1984).
Slaptopolsky, E. et al., *J. Clin. Invest* 50:492–499 (1971).
Slatopolsky, E. et al., *Am. Soc. Nephrol* 6:971 (1995).
Clarkson, E.M. et al., *Clin. Sci.* 30:425–438 (1966).
Coburn, J.W. et al., *Kidney Int* 4:96–104 (1973).
Lau, K. et al., *Fluids And Electrolytes*, W.B. Saunders Company, Second Edition, Philadelphia, Ch. 8–pp. 505–571 (1990).

*Primary Examiner*—Keith MacMillan
*Attorney, Agent, or Firm*—Harness, Dickey & Pierce, P.L.C.

[57] ABSTRACT

Methods of controlling phosphate metabolism and metabolic acidosis in patients suffering from renal failure and associated hyperphosphatemia or patients predisposed to development of a hyperphosphatemic condition are provided. The method in accordance with this invention comprises administering to a patient a ferric-containing compound selected from the group consisting of ferric citrate, ferric acetate, and combinations thereof. Therapeutic benefit can be realized in accordance with such method by administering the compound orally to a patient to contact and bind with ingested phosphate in the patient's digestive tract, and thereby prevent its intestinal absorption.

13 Claims, No Drawings

METHODS FOR TREATING RENAL FAILURE

FIELD OF THE INVENTION

The present invention relates generally to the control of phosphate retention and particularly, to methods for treating patients suffering from renal failure and associated hyperphosphatemia.

BACKGROUND OF THE INVENTION

Phosphate is primarily excreted through the kidney. Phosphate retention therefore inevitably occurs in renal failure. Phosphate restriction plays an important role in slowing down deterioration of renal function as well as soft tissue calcification in renal failure. A high intake of dietary phosphorus in experimental renal failure worsens renal function (Haut, L. L., Kidney Int 17:722–731 (1980); Karlinsky, D. et al., Kidney Int 17:293–302 (1980)) and a low phosphate intake arrests progression of chronic renal failure. Lumlertgul, D. et al., Kidney Int 29:658–666 (1986). Recent studies have demonstrated that phosphate restriction either increases plasma calcitriol (the most potent vitamin D metabolite) and suppresses secondary hyperparathyroidism (Portale, A. A. et al., J. Clin. Invest 73:1580–1589 (1989); Kilav, R. et al., J Clin. Invest 96:327–333 (1995); Lopez, H. et al., Am. J Physiol 259:F432–437 (1990)), or directly inhibits parathyroid cell proliferation. Naveh-Many, T. et al., Am. Soc. Nephrol 6:968 (1995). Taken together, maintaining a normal plasma concentration and tissue content of phosphate is an important means to prevent secondary hyperparathyroidism, renal osteodystrophy and soft tissue calcification in renal failure.

Dietary restriction of phosphate is difficult to achieve and thrice weekly dialysis alone can not remove daily absorbed phosphate. Therefore, phosphate binding agents have generally been employed to control phosphate metabolism in renal failure. For the last 30 years nephrologist have been using aluminum carbonate or aluminum hydroxide as phosphate binding agents. Concerns about aluminum toxicity in renal failure have prompted increased use of calcium carbonate and calcium acetate and a cessation in the use of aluminum compounds. However, calcium carbonate or other calcium preparations are not only inadequate to remove all the ingested dietary phosphate, but also provide too much calcium to end stage renal disease (ESRD) patients.

In 1943, ferric ammonium citrate was used in two patients with chronic renal failure for several months to lower the plasma phosphate. Liu, S. H., et al., Medicine, Baltimore 22:1031–1061 (1943). The side effect reported was diarrhea. However, ferric ammonium citrate may not be an ideal compound because it contains a large amount of ammonium when used in therapeutic doses (4 to 12 gm per day). The ammonia released from this compound could lead to side effects such as irritating the stomach and intestine. Further, this compound is not safe to use in renal failure patients with liver diseases as it may lead to hepatic coma.

In addition, animal studies have demonstrated that while both aluminum and ferric salts reduce plasma phosphate and urinary phosphate excretion, they also drastically reduced bone ash and bone phosphorus. Cox, G. et al., J. Biol. Chem 92:Xi–Xii (1931). For example, growing rats fed with ferric salts had growth retardation, hypophosphatemia, considerable loss of bone ash and total body content of calcium and phosphorus. The rats developed rickets within one month in severe phosphate restriction. Brock, J. et al., J. Pediat 4:442–453 (1934); Rehm, P. et al., J. Nutrition 19:213–222 (1940). Ferric salts also produced severe rickets and hypophosphatemia in one-day old chicks. Deobald, H. et al., Am. J. Physiol 111:118–123 (1935).

There is thus recognized in the medical community an urgent need for the development of a phosphate binder efficient in binding phosphate in renal failure. Accordingly, it is one object of this invention to provide a method for controlling hyperphosphatemia and phosphate retention utilizing a phosphate binding compound. It is another object of this invention to provide a method for correcting metabolic acidosis in renal failure. It is yet another object of this invention to provide a composition in an oral dosage form for inhibiting the absorption of dietary phosphate and/or correcting metabolic acidosis.

SUMMARY OF THE INVENTION

In accordance with this invention, ferric-containing compounds including ferric citrate and ferric acetate, are employed as agents for preventing absorption of ingested phosphates in the digestive tract. The compounds may also be employed as agents for correcting metabolic acidosis. The compounds can be utilized in accordance with this invention in an oral dosage form to bind and thereby prevent absorption of ingested phosphate from the intestine. It is believed that a 1 gram dose of ferric citrate and/or ferric acetate can bind approximately 40 mg of phosphorus.

The methods of the present invention may therefore be used to reduce phosphate retention and correct metabolic acidosis in renal failure. Moreover, absorption of iron from the ferric-containing compounds is also beneficial in the treatment of patients with renal failure, as anemia and iron deficiency frequently occurs in renal failure, especially in patients receiving erythropoietin.

Without wishing to be bound by theory, it is believed that ferric citrate and ferric acetate react with phosphate and precipitate phosphate as ferric phosphate or ferrous phosphate which is insoluble and not absorbable in the intestine. It is also believed that the absorbed citrate from either the ferric citrate or the ferric acetate which is converted to citrate, is converted to bicarbonate which corrects metabolic acidosis.

Other features and advantages of the present invention will become apparent from the following description and appended claims.

DETAILED DESCRIPTION OF THE PREFERRED EMBODIMENTS

Methods of controlling serum phosphate levels and metabolic acidosis in patients suffering from renal failure and associated hyperphosphatemia or patients predisposed to development of a hyperphosphatemic condition are provided. The method in accordance with this invention comprises administering to a patient a ferric-containing compound selected from the group consisting of ferric citrate, ferric acetate, and combinations thereof. Therapeutic benefit can be realized in accordance with such method by administering the compound orally to a patient to bind ingested phosphate in the patient's digestive tract, and thereby prevent intestinal absorption.

In a preferred embodiment of this invention, the ferric-containing compounds are formulated as a therapeutic dosage form for oral administration to a patient afflicted with hyperphosphatemia or predisposed to develop that condition. Thus, the ferric-containing compounds can be formulated as a liquid or gel suspension, or in a unitary solid dosage form such as a compressed tablet or capsule. Methods and excipients for preparation of both gel and solid dosage forms are well known in the art. It will be appreciated that the composition of the present invention may also be employed in a pharmaceutically-acceptable form such as an ester, salt, or as a pro-drug.

The oral dosage form should be formulated to contain sufficient ferric-containing compound to bind, upon ingestion by the patient, sufficient ingested phosphate in the patient's intestinal tract to inhibit the absorption of ingested phosphate and thereby reduce the probability of either the development of a hyperphosphatemic condition or the complication of an already existing hyperphosphatemic condition. Thus, each oral dose of the therapeutic ferric-containing composition in accordance with this invention can contain from about 500 mg to about 1000 mg of ferric-containing compound. A therapeutically-effective amount of the ferric-containing compounds to be administered will depend on the severity of the patient's condition, the nature of the patient's diet and the binding capacity of the ferric-containing compound used in the formulation. By "therapeutically-effective amount" is meant an amount effective to achieve a selected desired result in accordance with the present invention, without undue adverse physiological effects or side effects; the desired result generally being a clinically observable reduction in absorption of ingested phosphate and/or a correction in metabolic acidosis. The dosages of the compounds to be administered in accordance with this invention can thus be altered, if necessary, to correspond to the level of phosphate binding required in the patient's digestive tract. A daily dosage of about 5 g to about 10 g is expected to be effective.

As discussed in detail below, in in vivo studies utilizing rats, approximately 1 g of iron ($Fe^{+++}$) binds approximately 130 mg and 180 mg of phosphorus in normal and renal failure rats, respectively, or 1 g of ferric citrate binds 30 mg and 40 mg of phosphorus in normal and renal failure rats, respectively. Each animal consumed approximately 24 g of food which contains 220 mg of iron daily. It is believed that ferric citrate and ferric acetate will have the same binding potency in human subjects. Moreover, ingestion of 4 g ferric-containing compound per kg of rat, did not cause adverse effects.

It should be appreciated that while this invention preferably contemplates oral administration of the composition of the present invention, nothing herein should be construed to limit the mode of delivery. Both oral and systemic routes of delivery may be appropriate. Moreover, combination-therapy regimes are also contemplated by the present invention. It will also be appreciated that the compounds utilized in the compositions and methods of the present invention can be administered in accordance with the present invention in any pharmaceutically-acceptable carrier, preferably one which is both non-toxic and suitable for the specific mode of delivery. The compounds may be formulated for administration by procedures well-established in the pharmaceutical arts.

The foregoing and other aspects of the invention may be better understood in connection with the following examples, which are presented for purposes of illustration and not by way of limitation.

SPECIFIC EXAMPLE 1

Materials and Methods
Phosphate binding effect of ferric citrate in normal rats.

Male normal Sprague-Dawley rats (N=6) were fed with normal rat powder diet containing 1.02% P and 0.95% Ca (ICN Biomedicals Inc. Cleveland, Ohio) for two weeks. The content of P in the diet was verified. Powder food was used to prevent food contamination of urine and stool. Another six normal rats were fed with the same diet but containing 4% ferric citrate for two weeks. All animals were housed in each individual metabolic cages. Each rat's body weight, urine output, stool excretion and food consumption were monitored daily for 2 weeks four days per week. Weekly data of daily stools and urines were pooled together and expressed as an average per day for each week. Blood was taken once weekly for measurements of plasma phosphorus, creatinine and at the end of the study blood parathyroid hormone [PTH], calcitriol and iron concentrations as well. Phosphate binding effect of ferric compounds in rats with renal failure.

The phosphate binding effects of the ferric compounds was studied in rats with renal failure. Renal failure was achieved by subtotal nephrectomies. Two thirds of one kidney were removed surgically and the other kidney was removed through flank incision three days later. The renal function was reduced in these animals to about 50% of the normal. Renal failure was similar among the four groups of animals throughout the observations. Animals were divided in four groups [each group=7 rats]. Control group rats were fed for 4 weeks with normal powder rat diet containing 1.02% P and 0.95% Ca as above. The other three groups of animals were fed for 4 weeks with a diet containing 5% ferric ammonium citrate [contains 16.5–18.5% Fe], 4.4% $FeCl_3 6H_2O$ [M.W. 270.2], or 4% ferric citrate [$FeC_6H_5O_7$, M.W. 245], respectively. All the latter three diets contain 0.95 g Fe per 100 g food. Each rat's body weight, urine output, stool excretion and food consumption were monitored daily for 4 weeks, four days per week. Weekly data of daily stools and urines were pooled together and expressed as an average per day of each week. Blood was taken once weekly for measurements of plasma phosphorus, creatinine and at the end of the study blood parathyroid hormone [PTH], calcitriol and iron concentrations as well.
Analytical methods .

Stools were ashed at 800° C. in a muffled furnace for 30 min. and stool phosphorus was extracted with 10% perchloric acid overnight before phosphorus measurement. Phosphorus and creatinine were measured as described previously. Hsu, C., et al., *Kidney Int* 25:789–795 (1984). Plasma calcitriol was measured in duplicate according to the methods of Reinhardt et al. (Reinhardt, T. A. et al., *J. Clin. Endocrinol Metab* 58:91–98 (1984)) and Hollis. Hollis, B. W. et al., *Clin. Chem.* 32:2060–2063 (1986)). Interassay coefficients of variation were 7.0% for low control (20 pg/ml, N=12) and 4.1% for high control (100 pg/ml, N=12). The intraassay coefficients of variation were 5.4% for low control (N=6) and 4.7% for high control, respectively. Calcitriol recovery averaged 65%. PTH was measured by immunoradiometric assay (IRMA) using rat PTH assay kit (Nichols Institute, Capistrano, Calif.).

All data were expressed as mean±sem. Statistical analysis was performed using ANOVA with repeated measures and Fisher's PLSD tests. A p value of <0.05 was considered significant.

Results
Phosphate binding effect of ferric citrate in normal rats.

Both groups of animals grew at the same rate. They weighed similarly before and after two weeks of treatment [before treatment control, 264±2.9 g; treated, 269±3.7 g, after treatment control, 313±4.7 g; treated, 319±3.5 g]. All the rats (N=12) consumed equal amounts of food averaged 24 g per day [daily consumption of phosphorus control, 240.8±6.1 mg/day vs. treated, 240.2+7.2 mg/day]. From day one and throughout the experiment, the daily urinary excretion of phosphorus in the experimental group [eating diet containing ferric citrate] decreased by more than 50% at the end of the first week [control, 71.4±2.5 mg/day vs. treated, 30.4±2.6 mg/day, P<0.01] and at the end of the second week [control, 75.7±4.0 mg/day vs. treated, 30.7±1.5 mg/day, P<0.01]. The average daily urinary creatinine excretions were not different between the two groups of animals [first week: control, 8.72±0.38 mg/day vs. treated, 8.95±0.80 mg/day; second week: control, 9.99±0.43 mg/day vs. treated, 9.44±0.64 mg/day]. The reduction of urinary excretion of phosphate reflects decreased intestinal absorption of phosphate as the excretion of the stool phosphate increased by approximately 30 mg/day in rats eating diet containing ferric citrate [average daily stool P excretion control, first week, 135±4.1 mg/day vs. treated, 164±10.7 mg/day, P<0.03. Control, second week, 136±5.2 mg/day vs. treated, 163±1.7 mg/day, P<0.007]. From these data it was estimated that one gram of $Fe^{+++}$ binds approximately 130 mg phosphorus or one gram of ferric citrate binds 30 mg of phosphorus. Blood PTH [control, 16.2±3.8 pg/ml vs. treated, 16.0±3.5 pg/ml], calcitriol [control, 83.5±1.5 pg/ml vs. treated, 82.2±2.0 pg/ml], iron [control, 1.76±0.17 ug/ml vs. treated 1.73±12 ug/ml], hematocrit [control, 48.8±0.5% vs. treated, 47.8±0.7%] and phosphorus values were not different between the two groups of animals. The results of similar plasma iron concentrations in these animals suggest that iron is not absorbed in normal rats during the two weeks of experiment.

Phosphate binding effect of ferric compounds in rats with renal failure.

The results of the phosphate binding effects of these ferric compounds were similar to the previous study conducted in normal rats. However, on day 22 (4th week), two animals, one in the ferric ammonium citrate group and the other in the ferric citrate group were killed because of respiratory tract infection. Animals fed with either a diet containing ferric ammonium citrate or ferric citrate grew at the same rate as the control animals [Table 1]. However, the animals fed with a diet containing ferric chloride tended to grow slower than the control animals despite consuming equal amounts of food [Table 2] and phosphorus [Table 3].

TABLE 1

Weekly Average Weight

| Ex-periment | First Week (g) | Second Week (g) | Third Week (g) | Fourth Week* (g) |
|---|---|---|---|---|
| Control | 234.9 ± 8.7 | 268.0 ± 13.5 | 309.5 ± 13.5 | 336.1 ± 14.6 |
| FeNH$_4$ Citrate | 226.0 ± 7.3 | 260.2 ± 10.0 | 296.4 ± 14.2 | 333.3 ± 14.4 |
| FeCl$_3$ | 229.2 ± 9.4 | 250.6 ± 10.4 | 269.2 ± 11.4* | 296.3 ± 12.5* |
| Fe Citrate | 243.6 ± 7.8 | 266.6 ± 5.9 | 306.9 ± 8.8 | 345.7 ± 8.1 |

*Values were significantly lower than the controls (all P values were less than 0.05 or less).
FeNH$_4$ citrate: ferric ammonium citrate; Fe citrate: ferric citrate.
*Indicates N = 6 for FeNH$_4$ citrate and Fe citrate groups at the 4th week.

TABLE 2

Weekly Average Daily Food Intake

| Ex-periment | First Week (g/day) | Second Week (g/day) | Third Week (g/day) | Fourth Week* (g/day) |
|---|---|---|---|---|
| Control | 18.8 ± 1.3 | 20.8 ± 1.8 | 22.6 ± 1.1 | 22.2 ± 1.1 |
| FeNH$_4$ Citrate | 20.3 ± 1.1 | 23.0 ± 1.6 | 23.5 ± 1.7 | 23.1 ± 1.5 |
| FeCl$_3$ | 18.1 ± 0.5 | 20.4 ± 1.0 | 21.3 ± 0.7 | 21.4 ± 0.7 |
| Fe Citrate | 21.3 ± 0.9 | 23.3 ± 0.9 | 24.3 ± 0.9 | 24.8 ± 0.5 |

*Indicates N = 6 for FeNH$_4$ citrate and Fe citrate groups at the 4th week.

TABLE 3

Weekly Average Daily Phosphorus Intake

| Ex-periment | First Week (mg/day) | Second Week (mg/day) | Third Week (mg/day) | Fourth Week* (mg/day) |
|---|---|---|---|---|
| Control | 193.3 ± 13.4 | 214 ± 18.8 | 232.6 ± 11.6 | 228.0 ± 11.3 |
| FeNH$_4$ Citrate | 198.5 ± 10.8 | 224.8 ± 15.4 | 230.4 ± 16.7 | 205.0 ± 25.1 |
| FeCl$_3$ | 178.0 ± 4.6 | 201.0 ± 10.3 | 210.3 ± 7.1 | 210.5 ± 7.1 |
| Fe Citrate | 210.8 ± 9.6 | 230.6 ± 9.0 | 240.1 ± 9.9 | 245.6 ± 5.9 |

*Indicates N = 6 for FeNH$_4$ citrate and Fe citrate groups at the 4th week.

The urinary excretion of phosphate decreased immediately following the consumption of diets containing ferric compounds. The average daily urinary creatinine excretions were not different among the four groups of animals except the excretions were lower in FeCl$_3$ group at the third and fourth week compared to the controls. The values were significantly lower than those of controls throughout the four weeks of experiment [Table 5]. In contrast, daily stool phosphate excretion increased throughout the entire periods in rats fed with ferric diets [Table 6]. From the results of stool phosphorus excretion, it was estimated that one gram of $Fe^{+++}$ binds approximately 180 mg phosphorus or one gram of ferric citrate binds 40 mg of phosphorus in renal failure rats. Thus, it has been shown that ferric compounds effectively bind intestinal phosphate and reduce its absorption in animals with renal failure. The ferric-containing compounds of the present invention can thus be used in human subjects suffering from renal failure to reduce intestinal absorption of phosphate.

TABLE 4

Weekly Average Daily Creatinine Excretion

| Ex-periment | First Week (mg/day) | Second Week (mg/day) | Third Week (mg/day) | Fourth Week* (mg/day) |
|---|---|---|---|---|
| Control | 8.63 ± 0.70 | 9.81 ± 0.63 | 11.62 ± 0.81 | 12.90 ± 0.96 |
| FeNH$_4$ Citrate | 8.96 ± 0.60 | 10.28 ± 0.74 | 11.38 ± 0.83 | 11.79 ± 0.87 |
| FeCl$_3$ | 8.39 ± 0.37 | 8.86 ± 0.38 | 9.27 ± 0.51* | 10.73 ± 0.48* |
| Fe Citrate | 9.69 ± 1.26 | 10.59 ± 0.57 | 12.08 ± 0.61 | 12.79 ± 0.50 |

*Indicates N = 6 for FeNH$_4$ citrate and Fe citrate groups at the 4th week.
*p < 0.05 compared to Control.

TABLE 5

Weekly Average Daily Urinary Phosphate Excretion

| Ex-periment | First Week (mg/day) | Second Week (mg/day) | Third Week (mg/day) | Fourth Week* (mg/day) |
|---|---|---|---|---|
| Control | 61.8 ± 5.2 | 60.4 ± 5.9 | 65.7 ± 3.9 | 67.8 ± 3.6 |
| FeNH$_4$ Citrate | 28.3 ± 2.2* | 24.8 ± 2.8* | 25.5 ± 3.2* | 23.9 ± 2.1* |
| FeCl$_3$ | 30.8 ± 1.5* | 25.0 ± 1.7* | 17.3 ± 2.6* | 23.1 ± 1.8* |
| Fe Citrate | 33.1 ± 3.4* | 25.7 ± 2.2* | 28.1 ± 1.7* | 30.7 ± 1.6* |

*Indicates all P values are less than 0.05 or less.
*Indicates N = 6 for FeNH$_4$ citrate and Fe citrate groups at the 4th week.

TABLE 6

Weekly Average Daily Stool Phosphate Excretion

| Ex- periment | First Week (mg/day) | Second Week (mg/day) | Third Week (mg/day) | Fourth Week# (mg/day) |
|---|---|---|---|---|
| Control | 89.3 ± 9.9 | 111.6 ± 10.1 | 137.8 ± 9.1 | 140.4 ± 7.4 |
| FeNH$_4$ Citrate | 128.9 ± 6.6* | 148.4 ± 9.7* | 167.2 ± 10.5* | 170.6 ± 12.1* |
| FeCl$_3$ | 112.1 ± 3.3* | 145.9 ± 5.7* | 157.3 ± 6.0 | 162.5 ± 8.3 |
| Fe Citrate | 133.5 ± 6.5* | 156.3 ± 6.7* | 166.8 ± 4.7* | 182.8 ± 4.7* |

*Indicates all P values are less than 0.05 or less.
Indicates N = 6 for FeNH$_4$ citrate and Fe citrate groups at the 4th week.

Blood concentrations of phosphate were within normal ranges in these animals, as shown previously, this degree of renal failure does not raise plasma concentration of phosphate [Table 7]. Hsu, C. H. et al., *Kidney Int* 37:44–50 (1990). Blood concentrations of PTH in these four groups of renal failure animals were significantly higher than those of normal animals. Further, among the four groups of renal failure animals, the control renal failure animals had higher PTH levels compared to the other groups of animals, though the values did not reach statistical significance due to great variation in the control group [Table 8]. Plasma concentrations of creatinine were not different among the four groups of animals, whereas plasma concentrations of calcitriol tended to be lower in animals eating FeCl$_3$ diet.

TABLE 7

Plasma Concentrations Of Phosphorus Before And After Ferric Diets

| Ex- periment | Pre- treatment (mg/dl) | First Week (mg/dl) | Second Week (mg/dl) | Third Week (mg/dl) | Fourth Week# (mg/dl) |
|---|---|---|---|---|---|
| Control | 6.68 + 0.19 | 7.79 + 0.33 | 6.56 + 0.18 | 6.72 + 0.25 | 7.18 + 0.60 |
| FeNH$_4$ Citrate | 6.04 + 0.50 | 7.23 + 0.32 | 6.72 + 0.33 | 5.85 + 0.22 | 6.11 + 0.13 |
| FeCl$_3$ | 6.85 + 0.22 | 7.24 + 0.42 | 6.52 + 0.26 | 6.32 + 0.20 | 6.14 + 0.23 |
| Fe Citrate | 6.30 + 0.15 | 6.94 + 0.27 | 7.09 + 0.13 | 6.22 + 0.13 | 6.29 + 0.16 |

Indicates N = 6 for FeNH$_4$ citrate and Fe citrate groups at the 4th week

TABLE 8

Plasma Creatinine, Calcitriol And PTH Concentrations

| Experiment | *Plasma Creatinine | *Plasma Calcitriol | *PTH pg/ml |
|---|---|---|---|
| Control | 0.89 ± 0.10 | 54.2 ± 2.8 | 112.9 ± 57 |
| FeNH$_4$ Citrate# | 0.81 ± 0.05 | 56.1 ± 2.2 | 31.2 ± 8.1 |
| FeCl$_3$ | 0.76 ± 0.05 | 45.9 ± 3.8 | 22.4 ± 3.3 |
| Fe Citrate# | 0.80 ± 0.06 | 55.5 ± 1.6 | 28.0 ± 4.1 |

*These values were measured at the end of the 4 weeks balance studies.
Indicates N = 6 for FeNH$_4$ citrate and Fe citrate groups at the 4th week.

Table 9 summarizes the results of plasma iron concentration and hematocrit of the four groups of animals measured at the end of the four week study. Plasma concentrations of iron were significantly higher in the renal failure rats fed with ferric citrate diet compared to the controls fed with regular food. The other groups of animals fed with ferric compounds tend to have increased plasma iron concentrations though they did not achieve statistical significance. However, blood hematocrit values were significantly higher in animals fed with ferric compounds than in animals fed with regular diet. Apparently, small quantities of these ferric compounds, especially ferric citrate, are absorbed in the intestine.

TABLE 9

Plasma Concentration Of Iron And Blood Hematocrit

| Experiment | Iron (ug/ml) | Hematocrit % |
|---|---|---|
| Control | 1.26 ± 0.09 | 40.0 ± 4.4 |
| FeNH$_4$ Citrate# | 1.57 ± 0.21 | 44.7 ± 1.0*** |
| FeCl$_3$ | 1.70 ± 0.09 | 44.8 ± 0.6*** |
| Fe Citrate# | 2.10 ± 0.29** | 43.3 ± 0.6* |

*P < 0.04, P < 0.02, *P < 0.01 vs. control.
Indicates N = 6 for FeNH$_4$ citrate and Fe citrate groups at the 4th week.

Discussion

Kidney is the primary route for phosphate excretion, therefore, phosphate retention is a common problem in patients with renal failure. Dietary restriction of phosphate is difficult to achieve and thrice weekly dialysis alone can not remove daily absorbed phosphate. Hou, S. H. et al., *Am. J. Kidney Dis* 18:217–224 (1991). Consequently, phosphate binding agents (e.g., calcium carbonate or other calcium preparations) have generally been employed to control phosphate metabolism in renal failure. However, using these agents provides excessive calcium to end stage renal disease (ESRD) patients. Ramirez, J. A. et al., *Kidney Int* 30:753–759 (1986). It should be noted that most of the patients with ESRD have positive calcium balances as they have no route of calcium excretion. For example [Table 10], excluding dietary calcium absorption in the ESRD patients, one can expect positive calcium fluxes of average +896 mg/4 hours (+384 mg/day) and +150 mg/4 hours (+64 mg/day) thrice weekly hemodialysis, respectively, when using 3.5 mEq/l and 2.5 mEq/l calcium dialysate. Hou, S. H. et al., *Am. J. Kidney Dis* 18:217–224 (1991). Similarly, peritoneal dialysate with 3.5 mEq/l and 1.5% dextrose provides positive calcium fluxes of an average 14 mg/exchange or approximately 56 mg/day in normocalcemic patients [Table 11]. Martis, L., et al., *Perit Dial Int* 9:325–328 (1989); Piraino, B. et al., *Clin. Nephrol* 37:48–51 (1992). Assuming the ESRD patients consume an 800 mg/day of dietary calcium and an estimated fractional calcium absorption of 19% (Ramirez, J. A. et al., *Kidney Int* 30:753–759 (1986)), the calculated daily calcium balances for the adult ESRD patients would exceed the average normal calcium threshold balance of 114 mg/day for age 18 to 30 estimated by Matkovic and Heaney. Matkovic, V. et al., *Am. J. Clin. Nutr.* 55:992–996 (1992). Addition of calcium carbonate or other calcium products as phosphate binding agents for the treatment of secondary hyperparathyroidism would further increase calcium absorption and retention, especially in patients greater than 30 years of age. Ramirez, J. A. et al., *Kidney Int* 30:753–759 (1986).

TABLE 10

Estimated Calcium Balance In Hemodialysis Patients

Calcium Balance Using 3.5 mEq/l Ca Dialysate

Positive Ca flux ~ +896 mg/4h dialysis or +2688 mg/wk (384 mg/day)*
Dietary intake of Ca ~ 800 mg/day**
Fractional absorption ~ 152 mg/day (19%)***
Total Ca balance ~ +536 mg/day Calcium Balance Using 2.5 mEq/l Ca Dialysate Positive Ca flux ~ +150 mg/4h dialysis or +450 mg/wk (64 mg/day)*
Dietary intake of Ca ~ 800 mg/day**

TABLE 10-continued

Estimated Calcium Balance In Hemodialysis Patients

Fractional absorption ~ 152 mg/day (19%)***
Total Ca balance ~ +216 mg/day

*Assuming three dialysis/week and Ca flux estimated from ref. Hou, S.H. et al., Am. J. Kidney Dis 18:217–224 (1991).
**Estimated daily dietary intake.
***Fractional Ca absorption estimated from ref. Coburn, J.W. et al., Kidney Int 3:264–272 (1973).

TABLE 11

Estimated Calcium Balance In Peritoneal Dialysis Patients

Calcium Balance Using 3.5 mEq/l Ca And 1.5% Dextrose Dialysate

Positive Ca flux ~ +14 mg/exchange or +56 mg/day*
Dietary intake of Ca ~ 800 mg/day**
Fractional absorption ~ 152 mg/day (19%)***
Total Ca balance ~ +208 mg/day

*Assuming four exchange/day and Ca flux estimated from ref. Piraino, B. et al., Clin. Nephrol 37:48–51 (1992).
**Estimated daily dietary intake.
***Fractional Ca absorption estimated from ref. Coburn, J.W. et al., Kidney Int 3:264–272 (1973).
****Assuming four exchange/day and Ca flux estimated from ref. Martis, L., et al., Perit Dial Int 9:325–328 (1989).

In normal adults, age 20 to 53 years, the daily phosphate balance is slightly negative or in equilibrium. Lakshmanan, F. L. et al., Am. J. Clin. Nutr. 1368–1379 (1984). Similar to calcium excretion, the kidney is the primary route for phosphate excretion. Plasma concentration of phosphate usually remains within normal ranges until glomerular filtration rate is below approximately 20 ml/min. The normal plasma phosphate in the presence of renal failure is due to increased phosphate excretion ensuing from evaluation of plasma PTH. However, the plasma phosphate levels may not accurately reflect total body phosphate content. Lau, K. et al., Philadelphia: Saunders 505–571 (1990).

Although net phosphorus absorption is not different between chronic dialysis patients and normal subjects, intestinal absorption of phosphorus is increased in dialysis patients if they receive calcitriol treatment (dietary phosphate absorption increased from 60% to 86%). Ramirez, J. A. et al., Kidney Int 30:753–759 (1986). During hemodialysis, phosphate efflux is approximately 1057 mg/dialysis or 3171 mg/week. Hou, S. H. et al., Am. J. Kidney Dis 18:217–224 (1991). The removal of phosphate through hemodialysis is therefore inadequate to eliminate the daily dietary absorption of phosphate (4,200 mg/week, assuming dietary intake of 1000 mg/day and fractional absorption of phosphate is 60% [Table 12]). Ramirez, J. A. et al., Kidney Int 30:753–759 (1986). It is estimated that each dialysis patient needs about 4 g to about 5 g of ferric citrate, ferric acetate or a combination thereof, per day, in order to achieve a normal phosphate metabolism.

TABLE 12

Estimated Phosphate Balance In Hemodialysis Patients

Phosphate Balance In Hemodialysis

Negative P flux ~ −1057 mg/4h dialysis or −3171 mg/wk (−453 mg/day)*
Dietary intake ~ 1000 mg/day**
Fractional P absorption ~ 60% or 600 mg/day***
Total P balance +147 mg/day

TABLE 12-continued

Estimated Phosphate Balance In Hemodialysis Patients

Phosphate Balance In Hemodialysis

*Assuming three dialysis/wk and P flux estimated from ref. Hou, S.H. et al., Am. J Kidney Dis 18:217–224 (1991).
**Estimated daily dietary intake.
***Fractional P absorption estimated from ref. Ramirez, J.A. et al., Kidney Int 30:753–759 (1986).

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the specification and following claims.

All patents and other publications cited herein are expressly incorporated by reference.

We claim:

1. A method of controlling phosphate retention in a patient suffering from hyperphosphatemia or a patient predisposed to development of a hyperphosphatemic condition, comprising the step of administering to the patient a therapeutically-effective amount of a compound selected from the group consisting of ferric citrate, ferric acetate and combinations thereof.

2. The method of claim 1, wherein the compound is administered to the patient orally.

3. The method of claim 1, wherein the compound is ferric citrate.

4. The method of claim 1, wherein the compound is ferric acetate.

5. The method of claim 1, wherein the therapeutically-effective amount of the compound is a unit dosage of about 500 mg to about 1000 mg.

6. A therapeutic composition in oral dosage form for controlling phosphate retention in patients having need for reduced absorption of dietary phosphate, said composition comprising on a per dose basis from about 500 mg to about 1000 mg of a compound selected from the group consisting of ferric citrate, ferric acetate and combinations thereof, and a pharmaceutically acceptable excipient for said oral dosage form.

7. The composition of claim 6, wherein the compound is ferric citrate.

8. The composition of claim 6, wherein the compound is ferric acetate.

9. A method of controlling serum phosphate metabolism and metabolic acidosis in a patient suffering from renal failure, comprising the step of administering to the patient a therapeutically-effective amount of a compound selected from the group consisting of ferric citrate, ferric acetate and combinations thereof.

10. The method of claim 9, wherein the compound is administered to the patient orally.

11. The method of claim 9, wherein the therapeutically-effective amount of the compound is a unit dosage of about 500 mg to about 1000 mg.

12. The method of claim 9, wherein the compound is ferric citrate.

13. The method of claim 9, wherein the compound is ferric acetate.

* * * * *

UNITED STATES PATENT AND TRADEMARK OFFICE
CERTIFICATE OF CORRECTION

PATENT NO. : 5,753,706
DATED : May 19, 1998
INVENTOR(S) : Chen Hsing Hsu

It is certified that error appears in the above-identified patent and that said Letters Patent is hereby corrected as shown below:

On the Title Page, insert the following heading and information:

--Related U.S. Application Data--
--[60] Provisional application No. 60/032,745 Dec. 16, 1996--

On the Title Page under Inventor, "Ann Harbor" should be --Ann Arbor--.

Column 4, line 56, "+" should be --$\pm$--.

Column 1, line 3, insert the following:
Cross Reference to Related Application Reference is made to and Priority claimed from U.S. Provisional Application Serial No. 60/032,745 filed Dec. 16, 1996, entitled Methods for Treating.

Signed and Sealed this

Sixteenth Day of February, 1999

Attest:

Attesting Officer

Acting Commissioner of Patents and Trademarks

UNITED STATES PATENT AND TRADEMARK OFFICE
CERTIFICATE OF CORRECTION

| | | |
|---|---|---|
| PATENT NO. | : 5,753,706 | Page 1 of 1 |
| APPLICATION NO. | : 08/794328 | |
| DATED | : May 19, 1998 | |
| INVENTOR(S) | : Chen Hsing Hsu | |

It is certified that error appears in the above-identified patent and that said Letters Patent is hereby corrected as shown below:

On the Title Page, insert the following heading and information:

--Related U.S. Application Data--
--[60] Provisional application No. 60/032,745 Dec. 16, 1996--

On the Title Page, under Inventor, "Ann Harbor" should be --Ann Arbor--.

Column 4, line 56, "+" should be --±--.

Column 1, line 3, insert the following:
Cross Reference to Related Application Reference is made to and Priority claimed from U.S. Provisional Application Serial No. 60/032,745 filed Dec. 16, 1996, entitled Methods for Treating Renal Failure.

This certificate supersedes Certificate of Correction issued February 16, 1999.

Signed and Sealed this

Tenth Day of July, 2007

JON W. DUDAS
*Director of the United States Patent and Trademark Office*